United States Patent [19]

Sugimoto et al.

[11] Patent Number: 4,564,617

[45] Date of Patent: * Jan. 14, 1986

[54] THEOPHYLLINE AND THEOBROMINE DERIVATIVES

[75] Inventors: Hachiro Sugimoto, Kawaguchi; Takaharu Nakamura, Abiko; Sachiyuki Hamazo; Yoshiharu Daiku, all of Tokyo; Toshyi Lgaraski, Saitama, Japan

[73] Assignee: Eisai Co., Ltd., Tokyo, Japan

[ * ] Notice: The portion of the term of this patent subsequent to Jan. 17, 2001 has been disclaimed.

[21] Appl. No.: 484,044

[22] Filed: Apr. 11, 1983

Related U.S. Application Data

[62] Division of Ser. No. 298,227, Aug. 31, 1981, Pat. No. 4,426,383.

[30] Foreign Application Priority Data

Sep. 4, 1980 [JP] Japan .................................. 55-121712
Sep. 4, 1980 [JP] Japan .................................. 55-121713

[51] Int. Cl.[4] .................... C07D 473/08; A61K 31/52
[52] U.S. Cl. .................... 514/265; 514/263; 514/252; 514/253; 544/267; 544/268; 544/269
[58] Field of Search ...................... 544/267, 268, 269; 424/253; 514/265, 263, 252, 253

[56] References Cited

U.S. PATENT DOCUMENTS 4,400,381 8/1983 Favier et al. .................... 424/253
4,426,383 1/1984 Sugimoto et al. .................... 424/253

FOREIGN PATENT DOCUMENTS 2083470A 3/1982 United Kingdom .

Primary Examiner—Nicholas S. Rizzo
Attorney, Agent, or Firm—Flynn, Thiel, Boutell & Tanis

[57] ABSTRACT

A novel compound has the following formula:

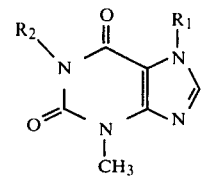

in which $R_1$ and $R_2$ are methyl or a group having the formula:

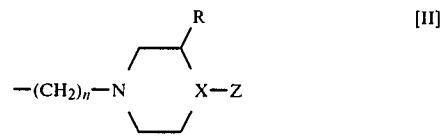

provided that one of $R_1$ and $R_2$ is methyl and the other is said group, wherein R stands for a hydrogen atom or a lower alkyl group, Z stands for a group

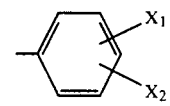

in which $X_1$ and $X_2$, which may be the same or different, stand for a hydrogen atom, a lower alkyl group, a lower alkoxy group, a trifluoromethyl group or a halogen atom, or a pyridyl group or a group

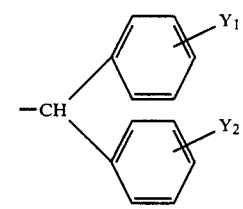

in which $Y_1$ and $Y_2$, which may be the same or different stand for a hydrogen atom, a lower alkyl group, a lower alkoxy group, a trifluoromethyl group or a halogen atom, X stands for a nitrogen or carbon atom, and n is an integer of from 2 to 10, provided that when $R_2$ is the group having the formula II, X is not carbon and Z is not pyridyl.

14 Claims, No Drawings

THEOPHYLLINE AND THEOBROMINE DERIVATIVES

This is a division of application Ser. No. 298,227, filed Aug. 31, 1981, now U.S. Pat. No. 4,426,383.

The present invention relates to a theophylline derivative and a theobromine derivative and then processes for manufacturing them. These compounds are novel and have excellent medicinal actions.

More particularly, the theophylline and theobromine derivatives have the following formula.

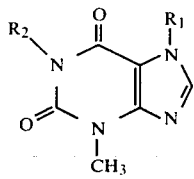
[I]

in which $R_1$ and $R_2$ are methyl or a group having the formula:

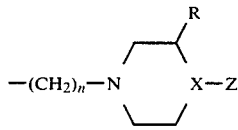
[II]

provided that one of $R_1$ and $R_2$ is methyl and the other is said group, wherein R stands for a hydrogen atom or a lower alkyl group, Z stands for a group

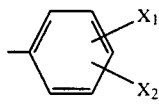

in which $X_1$ and $X_2$, which may be the same or different, stand for a hydrogen atom, a lower alkyl group, a lower alkoxy group, a trifluoromethyl group or a halogen atom, or a pyridyl group or a group

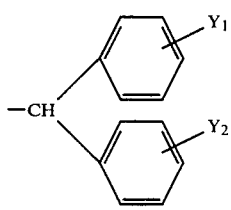

in which $Y_1$ and $Y_2$, which may be the same or different stand for a hydrogen atom, a lower alkyl group, a lower alkoxy group, a trifluoromethyl group or a halogen atom, X stands for a nitrogen or carbon atom, and n is an integer of from 2 to 10, provided that when $R_2$ is the group having the formula II, X is not carbon and Z is not pyridyl.

The invention includes an acid addition salt of the derivatives defined as above as well.

Among the compounds according to the invention, the theophylline derivatives have the following formula III.

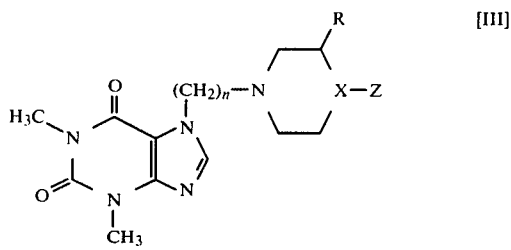
[III]

wherein R stand for a hydrogen atom or a lower alkyl group, Z stands for a group

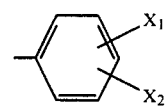

in which $X_1$ and $X_2$, which may be the same or different, stand for a hydrogen atom, a lower alkyl group, a lower alkoxy group, a trifluoromethyl group or a halogen atom, or a pyridyl group or a group

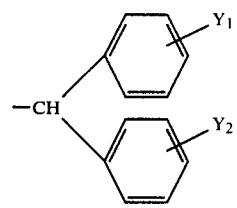

in which $Y_1$ and $Y_2$, which may be the same or different stand for a hydrogen atom, a lower alkyl group, a lower alkoxy group, a trifluoromethyl group or a halogen atom, X stands for a nitrogen or carbon atom, and n is an integer of from 2 to 10.

Then, the theobromine derivatives have the following formula IV.

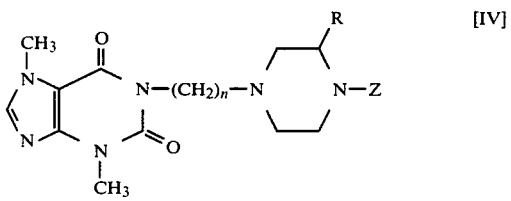
[IV]

wherein R stands for a hydrogen atom or a lower alkyl group, Z stands for a group

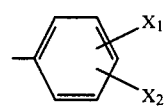

in which $X_1$ and $X_2$, which may be the same or different, stand for a hydrogen atom, a lower alkyl group, a lower alkoxy group, a trifluoromethyl group or a halogen atom, or a group

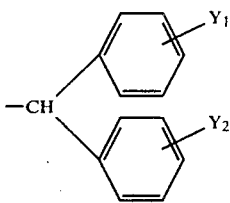

in which $Y_1$ and $Y_2$, which may be the same or different, stand for a hydrogen atom, a lower alkyl group, a lower alkoxy group, a trifluoromethyl group or a halogen atom, and n is an integer of from 2 to 10.

In the definitions of R, $X_1$, $X_2$, $Y_1$ and $Y_2$ of the general formula [I], by the term "lower alkyl group" are meant linear or branched alkyl groups having 1 to 6 carbon atoms, such as methyl, ethyl, n-propyl, isopropyl, isobutyl, 1-methylpropyl, tert-butyl, n-pentyl, 1-ethylpropyl, isoamyl and n-hexyl groups. By the term "lower alkoxy group" are meant alkoxy groups corresponding to the above-mentioned lower alkyl groups. As the halogen atom, there can be mentioned chlorine, bromine, iodine and fluorine.

Among theobromine derivatives defined as before, those having the formula IV in which Z is

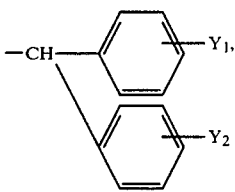

or Z is

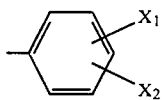

and n is 2,9 or 10 is preferable.

The compound [I] of the present invention can easily be converted to an acid addition salt by reaction with a pharmacologically acceptable inorganic or organic acid. As the inorganic acid, there can be mentioned hydrochloric acid, hydrobromic acid, hydroiodic acid and sulfuric acid, and as the organic acid, there can be mentioned maleic acid, fumaric acid, succinic acid, acetic acid, malonic acid, citric acid and benzoic acid.

Typical examples of the theophilline derivatives of the invention will now be mentioned, though the scope of the present invention is not limited by these examples.

7-{2-[4-p-chlorobenzhydrylpiperazinyl-(1)]ethyl}-theophylline
7-{3-[4-p-chlorobenzhydrylpiperazinyl-(1)]-n-propyl}-theophylline
7-{4-[4-p-chlorobenzhydrylpiperazinyl-(1)]-n-butyl}-theophylline
7-{5-[4-p-methylbenzhydrylpiperazinyl-(1)]-n-pentyl}-theophylline
7-{6-[4-p-methoxybenzhydrylpiperazinyl-(1)]-n-hexyl}-theophylline
7-{7-[4-o-trifluoromethylbenzhydrylpiperazinyl-(1)]-n-heptyl}-theophylline
7-{8-[4-benzhydrylpiperazinyl-(1)]-n-octyl}-theophylline
7-{9-[4-p-chlorobenzhydrylpiperazinyl-(1)]-n-nonyl}-theophylline
7-{10-[4-p-ethoxybenzhydrylpiperazinyl-(1)]-n-decyl}-theophylline
7-{4-[4-(4',4''-dichlorodiphenylmethyl)piperazinyl-(1)]-n-butyl}-theophylline
7-{2-[(4-phenyl)piperazinyl-(1)]ethyl}-theophylline
7-{3-[(4-phenyl)piperazinyl-(1)]-n-propyl}-theophylline
7-{4-[(4-phenyl)piperazinyl-(1)]-n-butyl}-theophylline
7-{5-[(4-phenyl)piperazinyl-(1)]-n-pentyl}-theophylline
7-{6-[(4-phenyl)piperazinyl-(1)]-n-hexyl}-theophylline
7-{2-[4-o-methylphenylpiperazinyl-(1)]-ethyl}-theophylline
7-{3-[4-o-methylphenylpiperazinyl-(1)]-n-propyl}-theophylline
7-{5-[4-o-methylphenylpiperazinyl-(1)]-n-pentyl}-theophylline
7-{2-[4-m-methylphenylpiperazinyl-(1)]-ethyl}-theophylline
7-{4-[4-m-methylphenylpiperazinyl-(1)]-n-butyl}-theophylline
7-{5-[4-m-methylphenylpiperazinyl-(1)]-n-pentyl}-theophylline
7-{6-[4-m-methylphenylpiperazinyl-(1)]-n-hexyl}-theophylline
7-{2-[4-(2,3-dimethylphenyl)piperazinyl-(1)]-ethyl}-theophylline
7-{2-[4-(2,6-dimethylphenyl)piperazinyl-(1)]-ethyl}-theophylline
7-{2-[4-(2,6-dimethylphenyl)piperazinyl-(1)]-n-propyl}-theophylline
7-{4-[4-(2,6-dimethylphenyl)piperazinyl-(1)]-n-butyl}-theophylline
7-{5-[4-(2,6-dimethylphenyl)piperazinyl-(1)]-n-pentyl}-theophylline
7-{6-[4-(2,6-dimethylphenyl)piperazinyl-(1)]-n-hexyl}-theophylline
7-{3-[4-(2,3-dimethylphenyl)piperazinyl-(1)]-n-propyl}-theophylline
7-{4-[4-(2,3-dimethylphenyl)piperazinyl-(1)]-n-butyl}-theophylline
7-{5-[4-(2,3-dimethylphenyl)piperazinyl-(1)]-n-pentyl}-theophylline
7-{6-[4-(2,3-dimethylphenyl)piperazinyl-(1)]-n-hexyl}-theophylline
7-{2-[4-(2,5-dimethylphenyl)piperazinyl-(1)]-ethyl}-theophylline
7-{3-[4-(2,5-dimethylphenyl)piperazinyl-(1)]-n-propyl}-theophylline
7-{4-[4-(2,5-dimethylphenyl)piperazinyl-(1)]-n-butyl}-theophylline
7-{5-[4-(2,5-dimethylphenyl)piperazinyl-(1)]-n-pentyl}-theophylline
7-{6-[4-(2,5-dimethylphenyl)piperazinyl-(1)]-n-hexyl}-theophylline
7-{2-[4-o-methoxyphenylpiperazinyl-(1)]-ethyl}-theophylline
7-{3-[4-o-methoxyphenylpiperazinyl-(1)]-n-propyl}-theophylline
7-{4-[4-o-methoxyphenylpiperazinyl-(1)]-n-butyl}-theophylline
7-{5-[4-o-methoxyphenylpiperazinyl-(1)]-n-pentyl}-theophylline 7-{6-[4-o-methoxyphenylpiperazinyl-(1)]-n-hexyl}-theophylline
7-{2-[4-m-methoxyphenylpiperazinyl-(1)]-ethyl}-theophylline
7-{3-[4-m-methoxyphenylpiperazinyl-(1)]-n-propyl}-theophylline
7-{4-[4-m-methoxyphenylpiperazinyl-(1)]-n-butyl}-theophylline
7-{5-[4-m-methoxyphenylpiperazinyl-(1)]-n-pentyl}-theophylline
7-{6-[4-m-methoxyphenylpiperazinyl-(1)]-n-hexyl}-theophylline
7-{2-[4-p-methoxyphenylpiperazinyl-(1)]-ethyl}-theophylline
7-{4-[4-p-methoxyphenylpiperazinyl-(1)]-n-butyl}-theophylline
7-{5-[4-p-methoxyphenylpiperazinyl-(1)]-n-pentyl}-theophylline
7-{6-[4-p-methoxyphenylpiperazinyl-(1)]-n-hexyl}-theophylline
7-{2-[4-o-chlorophenylpiperazinyl-(1)]-ethyl}-theophylline
7-{4-[4-o-chlorophenylpiperazinyl-(1)]-n-butyl}-theophylline
7-{5-[4-o-chlorophenylpiperazinyl-(1)]-n-pentyl}-theophylline
7-{6-[4-o-chlorophenylpiperazinyl-(1)]-n-hexyl}-theophylline
7-{2-[4-m-chlorophenylpiperazinyl-(1)]-ethyl}-theophylline
7-{4-[4-m-chlorophenylpiperazinyl-(1)]-n-butyl}-theophylline
7-{4-[4-m-chlorophenylpiperazinyl-(1)]-n-pentyl}-theophylline
7-{2-[4-o-chlorophenylpiperazinyl-(1)]-ethyl}-theophylline
7-{4-[4-o-chlorophenylpiperazinyl-(1)]-n-butyl}-theophylline
7-{5-[4-o-chlorophenylpiperazinyl-(1)]-n-pentyl}-theophylline
7-{6-[4-o-chlorophenylpiperazinyl-(1)]-n-hexyl}-theophylline
7-{2-[4-(3,4-dichlorophenyl)piperazinyl-(1)]-ethyl}-theophylline
7-{3-[4-(3,4-dichlorophenyl)piperazinyl-(1)]-n-propyl}-theophylline
7-{4-[4-(3,4-dichlorophenyl)piperazinyl-(1)]-n-butyl}-theophylline
7-{4-[4-p-fluorophenylpiperazinyl-(1)]-n-propyl}-theophylline
7-{5-[4-p-fluorophenylpiperazinyl-(1)]-n-butyl}-theophylline
7-{3-[4-m-trifluoromethylphenylpiperazinyl-(1)]-n-propyl}-theophylline
7-{4-[4-m-trifluoromethylphenylpiperazinyl-(1)]-n-butyl}-theophylline
7-{5-[4-m-trifluoromethylphenylpiperazinyl-(1)]-n-pentyl}-theophylline
7-{4-[4-o-trifluoromethylphenylpiperazinyl-(1)]-n-butyl}-theophylline
7-{3-[4-p-trifluoromethylphenylpiperazinyl-(1)]-n-propyl}-theophylline
7-{2-[4-(2-pyridyl)piperazinyl-(1)]-ethyl}-theophylline
7-{3-[4-(2-pyridyl)piperazinyl-(1)]-n-propyl}-theophylline
7-{4-[4-(2-pyridyl)piperazinyl-(1)]-n-butyl}-theophylline
7-{5-[4-(2-pyridyl)piperazinyl-(1)]-n-pentyl}-theophylline
7-{6-[4-(2-pyridyl)piperazinyl-(1)]-n-hexyl}-theophylline
7-{7-[(3-methyl-4-m-methylphenyl)piperazinyl-(1)]-n-heptyl}-theophylline
7-{2-[(3-methyl-4-phenyl)piperazinyl-(1)]-ethyl}-theophylline
7-{4-[(3-methyl-4-phenyl)piperazinyl-(1)]-n-butyl}-theophylline
7-{5-[(3-methyl-4-phenyl)piperazinyl-(1)]-n-pentyl}-theophylline
7-{2-[(3-methyl-4-p-methoxyphenyl)piperazinyl-(1)]-ethyl}-theophylline
7-{5-[(3-methyl-4-p-methoxyphenyl)piperazinyl-(1)]-n-pentyl}-theophylline
7-{6-[(3-ethyl-4-p-methoxyphenyl)piperazinyl-(1)]-n-hexyl-theophylline
7-{7-[4-m-chlorophenylpiperazinyl-(1)]-n-heptyl}-theophylline
7-{8-[4-(3,4-dimethylphenyl)piperazinyl-(1)]-n-octyl}-theophylline
7-{9-[4-(2,3-diethylphenyl)piperazinyl-(1)]-n-nonyl}-theophylline
7-{10-[4-m-ethoxyphenylpiperazinyl-(1)]-n-decyl}-theophylline
7-{7-[4-(2,3-dimethylphenyl)piperazinyl-(1)]-n-heptyl}-theophylline
7-{7-[4-(2-methyl-3-ethylphenyl)piperazinyl-(1)]-n-heptyl}-theophylline
7-{3-[4-(2-methyl-3-n-propylphenyl)piperazinyl-(1)]-n-propyl}-theophylline
7-{2-[(4-phenyl)piperidinyl]-ethyl}-theophylline
7-{3-[(4-phenyl)piperidinyl]-n-propyl}-theophylline
7-{4-[(4-phenyl)piperidinyl]-n-butyl}-theophylline
7-{5-[(4-p-chlorophenyl)piperidinyl]-n-pentyl}-theophylline
7-{5-[4-(3,4-dichlorophenyl)piperazinyl-(1)]-n-pentyl}-theophylline
7-{7-[4-(2-methyl-5-chlorophenyl)piperazinyl-(1)]-n-heptyl}-theophylline
7-{1-[(4-o-methoxyphenyl)piperazinyl-(1)]-n-decyl}-theophylline
7-{10-[4-(2-methyl-5-chlorophenyl)piperazinyl-(1)]-n-decyl}-theophylline
7-{10-[3-methyl-4-m-methylphenylpiperazinyl-(1)]-n-decyl}-theophylline
7-{10-[4-(3,4-dimethylphenyl)piperazinyl-(1)]-n-decyl}-theophylline Theophylline derivatives provided according to the present invention are novel compounds which have not been introduced in any of literature references. They have very high vasolidating and blood flow-increasing actions and they are effective for improving blood flows in the cerebral and coronary arteries and the capillary vessels. Furthermore, the compounds of the present invention have an action of controlling coagulation of blood platelets. Accordingly, they are suitable as agents for remedy of various diseases caused by troubles in blood flows in capillary vessels, cerebral blood vessel disorders and sequelae thereof, stenocardia and cardiac infraction. Moreover, theophylline derivatives provided according to the present invention are excellent in other various pharmacological actions such as the action to the central nervous system, the anti-histaminic action, the analgesic action, the anti-asthmatic action and the hypotensive action. Accordingly, the compounds of the present invention can effectively be used as psychic energizers, anti-histaminic agents, analgesic agents, anti-asthmatic agents and hypotensive agents.

Compounds [III] of the present invention can be prepared according to various processes. For example, a process represented by the following reaction formula is ordinarily adopted:

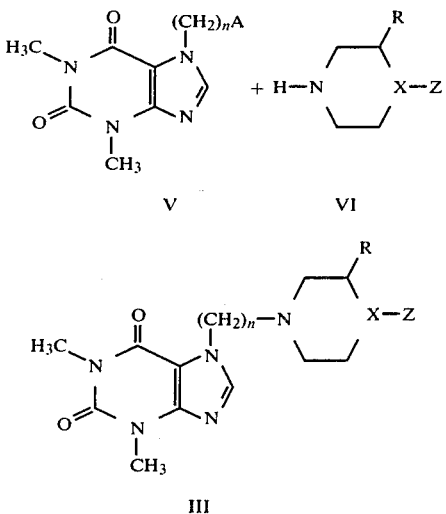

wherein A stands for a halogen atom or a p-toluene-sulfonyloxy group, and R, X, Z and n are as defined above.

In short, a compound III of the present invention can be obtained by reacting a compound represented by the general formula V with a compound represented by the general formula VI.

This reaction is carried out in the absence of a solvent or in the presence of a solvent not participating in the reaction, which is appropriately selected from lower alcohols such as methanol, ethanol, propanol and isopropanol, benzene type solvents such as benzene, toluene and xylene, and ethers such as ethyl ether and tetrahydrofuran. The reaction can be advanced even at room temperature, but it is preferred that the reaction be carried out at an elevated temperature of up to the boiling point of the solvent. The reaction can be performed more smoothly by adding an acid binder such as triethylamine, an alkali metal bicarbonate, an alkali metal carbonate or pyridine to the reaction mixture.

Typical examples of the theobromine derivatives of the invention will now be mentioned, though the scope of the present invention is not limited by these examples.

1-{7-[4-o-methoxyphenylpiperazinyl-(1)]-n-heptyl}-theobromine
1-{6-[4-o-methoxyphenylpiperazinyl-(1)]-n-hexyl}-theobromine
1-{5-[4-m-methoxyphenylpiperazinyl-(1)]-n-pentyl}-theobromine
1-{6-[4-m-methoxyphenylpiperazinyl-(1)]-n-hexyl}-theobromine
1-{8-[4-o-methoxyphenylpiperazinyl-(1)]-n-octyl}-theobromine
1-{10-[4-m-methoxyphenylpiperazinyl-(1)]-n-decyl}-theobromine
1-{2-[4-p-methoxyphenylpiperazinyl-(1)]-ethyl}-theobromine
1-{4-[4-o-ethoxyphenylpiperazinyl-(1)]-n-butyl}-theobromine
1-{4-[4-o,m-dimethylphenylpiperazinyl-(1)]-n-butyl}-theobromine
1-{2-[4-(2,6-dimethylphenyl)piperazinyl-(1)]-ethyl}-theobromine
1-{3-[4-(2,6-dimethylphenyl)piperazinyl-(1)]-n-propyl}-theobromine
1-{4-[4-(2,6-dimethylphenyl)piperazinyl-(1)]-n-butyl}-theobromine
1-{5-[4-(2,6-dimethylphenyl)piperazinyl-(1)]-n-pentyl}-theobromine
1-{2-[4-(2,3-dimethylphenyl)piperazinyl-(1)]-ethyl}-theobromine
1-{3-[4-(2,3-dimethylphenyl)piperazinyl-(1)]-n-propyl}-theobromine
1-{4-[4-(2,3-dimethylphenyl)piperazinyl-(1)]-n-butyl}-theobromine
1-{5-[4-(2,3-dimethylphenyl)piperazinyl-(1)]-n-pentyl}-theobromine
1-{6-[4-(2,3-dimethylphenyl)piperazinyl-(1)]-n-hexyl}-theobromine
1-{2-[4-(2,5-dimethylphenyl)piperazinyl-(1)]-ethyl}-theobromine
1-{3-[4-(2,5-dimethylphenyl)piperazinyl-(1)]-n-propyl}-theobromine
1-{4-[4-(2,5-dimethylphenyl)piperazinyl-(1)]-n-butyl}-theobromine
1-{5-[4-(2,5-dimethylphenyl)piperazinyl-(1)]-n-pentyl}-theobromine
1-{6-[4-(2,5-dimethylphenyl)piperazinyl-(1)]-n-hexyl}-theobromine
1-{7-[4-(2,5-dimethylphenyl)piperazinyl-(1)]-n-heptyl}-theobromine
1-{8-[4-(2,3-dimethylphenyl)piperazinyl-(1)]-n-octyl}-theobromine
1-{9-[4-(2,6-dimethylphenyl)piperazinyl-(1)]-n-nonyl}-theobromine
1-{10-[4-(2,5-dimethylphenyl)piperazinyl-(1)]-n-decyl}-theobromine
1-{5-[4-benzhydrylpiperazinyl-(1)]-n-pentyl-theobromine
1-{2-[4-benzhydrylpiperazinyl-(1)]-ethyl}-theobromine
1-{3-[4-benzhydrylpiperazinyl-(1)]-n-propyl}-theobromine
1-{4-[4-benzhydrylpiperazinyl-(1)]-n-pentyl}-theobromine
1-{5-[4-benzhydrylpiperazinyl-(1)]-n-pentyl}-theobromine
1-{6-[4-benzhydrylpiperazinyl-(1)]-n-hexyl}-theobromine
1-{2-[4-p-chlorobenzhydrylpiperazinyl-(1)]-ethyl}-theobromine
1-{3-[4-p-chlorobenzhydrylpiperazinyl-(1)]-n-propyl}-theobromine
1-{4-[4-p-chlorobenzhydrylpiperazinyl-(1)]-n-butyl}-theobromine
1-{5-[4-p-chlorobenzhydrylpiperazinyl-(1)]-n-pentyl}-theobromine
1-{6-[4-p-chlorobenzhydrylpiperazinyl-(1)]-n-hexyl}-theobromine
1-{10-[4-p-methoxybenzhydrylpiperazinyl-(1)]-n-decyl}-theobromine
1-{4-[4-(4',4''-dichlorophenylmethyl)piperazinyl-(1)]-n-butyl}-theobromine
1-{9-[4-p-chlorobenzhydrylpiperazinyl-(1)]-n-nonyl}-theobromine
1-{8-[4-p-methylbenzhydrylpiperazinyl-(1)]-n-octyl}-theobromine 1-{7-[4-p-trifluoromethylbenzhydrylpiperazinyl-(1)]-n-heptyl}-theobromine 1-{6-[4-o-methylphenylpiperazinyl-(1)]-n-hexyl}-theobromine 1-{2-[4-m-methylphenylpiperazinyl-(1)]-ethyl}-theobromine 1-{3-[4-p-methylphenylpiperazinyl-(1)]-n-propyl}-theobromine 1-{4-[4-m-methylphenylpiperazinyl-(1)]-n-butyl}-theobromine 1-{5-[4-p-methylphenylpiperazinyl-(1)]-n-pentyl}-theobromine 1-{7-[4-p-trifluoromethylpiperazinyl-(1)]-n-heptyl}-theobromine 1-{8-[4-p-ethoxyphenylpiperazinyl-(1)]-n-octyl}-theobromine 1-{2-[4-o-chlorophenylpiperazinyl-(1)]-ethyl}-theobromine 1{3-[4-p-chlorophenylpiperazinyl-(1)]-n-propyl}-theobromine 1-{4-[4-o-chlorophenylpiperazinyl-(1)]-n-butyl}-theobromine 1-{5-[4-p-chlorophenylpiperazinyl-(1)]-n-pentyl}-theobromine 1-{6-[4-m-chlorophenylpiperazinyl-(1)]-n-hexyl}-theobromine 1-{7-[4-p-methoxyphenylpiperazinyl-(1)]-n-heptyl}-theobromine 1-{3-[4-(3,4-dichlorophenyl)piperazinyl-(1)]-n-propyl}-theobromine 1-{4-[4-(3,4-dichlorophenyl)piperazinyl-(1)]-n-butyl}-theobromine 1-{5-[4-(3,4-dichlorophenyl)piperazinyl-(1)]-n-pentyl}-theobromine 1-{6-[4-(2,3-dichlorophenyl)piperazinyl-(1)]-n-hexyl}-theobromine 1-{7-[4-(2,5-dichlorophenyl)piperazinyl-(1)]-n-heptyl}-theobromine 1-{8-[4-(2,6-dichlorophenyl)piperazinyl-(1)]-n-octyl}-theobromine 1-{9-[4-(3,4-dichlorophenyl)piperazinyl-(1)]-n-nonyl}-theobromine 1-{10-[4-(3,4-dichlorophenyl)piperazinyl-(1)]-n-decyl}-theobromine 1-{2-[3-methyl-4-phenylpiperazinyl-(1)]-ethyl}-theobromine 1-{3-[3-methyl-4-phenylpiperazinyl-(1)]-n-propyl}-theobromine 1-{4-[3-methyl-4-phenylpiperazinyl-(1)]-n-butyl}-theobromine 1-{5-[3-methyl-4-phenylpiperazinyl-(1)]-n-pentyl}-theobromine 1-{6-[3-methyl-4-phenylpiperazinyl-(1)]-n-hexyl}-theobromine 1-{2-[3-methyl-4-p-methoxyphenylpiperazinyl-(1)]-ethyl}-theobromine 1-{3-[3-methyl-4-p-methoxyphenylpiperazinyl-(1)]-n-propyl}-theobromine 1-{4-[3-methyl-4-o-methoxyphenylpiperazinyl-(1)]-n-butyl}-theobromine 1-{5-[3-methyl-4-m-methoxyphenylpiperazinyl-(1)]-n-pentyl}-theobromine 1-{7-[4-p-fluorophenylpiperazinyl-(1)]-n-heptyl}-theobromine 1-{10-[3-methyl-4-m-methoxyphenylpiperazinyl-(1)]-n-decyl}-theobromine 1-{10-[4-(2,4-dimethylphenylpiperazinyl-(1)]-n-decyl}-theobromine Theobromine derivatives provided according to the present invention are novel compounds which have not been introduced in any of literature references. They have very high vasolidating and blood flow-increasing actions and they are effective for improving blood flows in the cerebral and coronary arteries and the capillary vessels. Furthermore, the compounds of the present invention have an action of controlling coagulation of blood platelets. Accordingly, they are suitable as agents for remedy of various diseases caused by troubles in blood flows in capillary vessels, cerebral blood vessel disorders and sequelae thereof, stenocardia and cardiac infraction. Moreover, theobromine derivatives provided according to the present invention are excellent in other various pharmacological actions such as the action to the central vervous system, the anti-histaminic action, the amalgesic action, the anti-asthmatic action and the hypotensive action. Accordingly, the compounds of the present invention can effectively be used as psychic energizers, anti-histaminic agents, analgesic agents, anti-asthmatic agents and hypotensive agents.

Compounds [IV] of the present invention can be prepared according to various processes. For example, a process represented by the following reaction formula is ordinarily adopted:

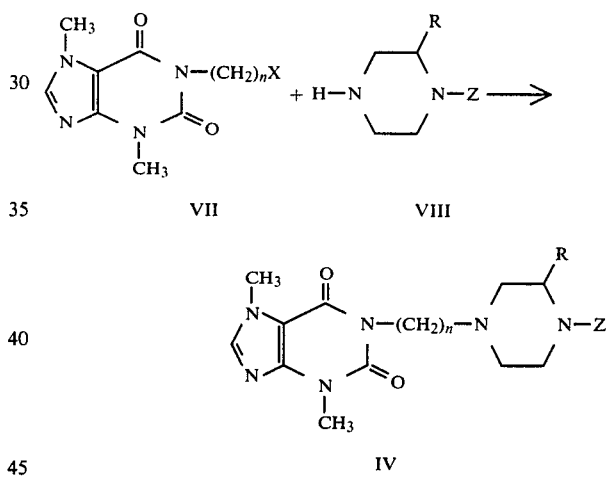

wherein X stands for a halogen atom or a p-toluene-sulfonyloxy group, and R, Z and n are as defined above.

In short, a compond IV of the present invention can be obtained by reacting a compound represented by the general formula VII with a compound represented by the general formula VIII.

This reaction is carried out in the absence of a solvent or in the presence of a solvent not participating in the reaction, which is appropriately selected from lower alcohols such as methanol, ethanol, propanol and isopropanol, benzene type solvents such as benzene, toluene and xylene, and ethers such as ethyl ether and tetrahydrofuran. The reaction can be advanced even at room temperature, but it is preferred that the reaction be carried out at an elevated temperature of up to the boiling point of the solvent. The reaction can be performed more smoothly by adding an acid binder such as triethylamine, an alkali metal bicarbonate, an alkali metal carbonate or pyridine to the reaction mixture.

Excellent physiological actions of the theophylline compound according to the invention will now be described with reference to typical compounds.

Blood Flow-Increasing Action

1. Methods

Male and female mongrel dogs having a body weight of 8 to 20 Kg were used as test animals, and the blood flows in the vertebral and femoral arteries were measured. More specifically, probes of an electromagnetic flow meter (Model MF-27 supplied by Nippon Koden) were attached to one side vertebral artery and one side femoral artery of a dog anesthetized by diethyl barbital (240 mg/kg, hypodermic injection) and sodium pentobarbital (10 mg/Kg, intravenous injection), and the blood flows of both the arteries were simultaneously measured. The test compound was administered by artery puncture at a dose of 0.1, 1 or 10 μg per Kg of the body weight.

2. Results:

The obtained results are shown in Table 2.

The intensity of the increase of the blood flow referred to in Table 2 was determined by using papaverine as a reference sample. The intensity of the sample having a minimum effective dose of 0.1 microgram/kg was designated as A and the intensity of the sample having a minimum effective dose of 1.0 microgram/kg was designated as B. Samples having a minimum effective dose of 10 microgram/kg were divided into two groups, one having an intensity higher than that of papaverine, and the intensity of the former group was designated as C and the intensity of the latter group was designated as D. The intensity of the sample having no activity was designated as E. Data of the increase of the blood flow and the duration of action, obtained with respect to 10 cases by using paraverine, are shown in Table 1.

TABLE 1

| | Dose (microgram/kg) | Increase in Blood Flow (mean ± SE) | Duration of Action (minutes) |
|---|---|---|---|
| Vertebral Artery | 1 | 0.3 ± 0.2 | 0.08 ± 0.05 |
| | 10 | 11.3 ± 2.7 | 0.55 ± 0.07 |
| Femoral Artery | 1 | 0.4 ± 0.3 | 0.09 ± 0.06 |
| | 10 | 12.6 ± 2.7 | 0.54 ± 0.07 |

TABLE 2

| Compound | | Class of Activity | Increase in Blood Flow (ml) | Duration of Action (minutes) | Dose (microgram/kg) |
|---|---|---|---|---|---|
| Compound 1 (theobromine deriv. with $(CH_2)_4$-piperazine-phenyl-OCH$_3$, .2HCl) | vertebral artery | A | 101 | 7.8 | 0.1 |
| | femoral artery | A | 27 | 1.7 | 0.1 |
| Compound 2 ($(CH_2)_4$-piperazine-CH(phenyl)(phenyl-Cl), .2HCl) | vertebral artery | D | 2 | 0.7 | 10 |
| | femoral artery | C | 16 | 0.7 | 10 |
| Compound 3 ($(CH_2)_5$-piperazine-phenyl, .2HCl) | vertebral artery | A | 4 | 0.6 | 0.1 |
| | femoral artery | A | 22 | 1.3 | 0.1 |
| Compound 4 ($(CH_2)_6$-piperazine-pyridyl, .3HCl) | vertebral artery | B | 4 | 0.5 | 1 |
| | femoral artery | B | 30 | 1.0 | 1 |

The theobromine derivatives were also examined in the same manner as described before in connection with the theophylline derivatives. Results are shown in Tables 3 and 4. From the results shown in Table 4, it will readily be understood that the compounds of the theobromine type have a very excellent blood flow-increasing action.

TABLE 3

| | Dose (microgram/kg) | Increase in Blood Flow (mean ± SE) (ml) | Duration of Action (minutes) |
|---|---|---|---|
| Vertebral Artery | 1 | 0.3 ± 0.2 | 0.08 ± 0.05 |
| | 10 | 11.3 ± 2.7 | 0.55 ± 0.07 |
| Femoral Artery | 1 | 0.4 ± 0.3 | 0.09 ± 0.06 |
| | 10 | 12.6 ± 2.7 | 0.54 ± 0.07 | hydroxide and is then extracted with chloroform. The chloroform layer is washed with water and dried with anhydrous potassium carbonate. The solvent is removed by distillation and the residual crude crystal is converted to a hydrochloride according to customary procedures. The hydrochloride is recrystallized from methyl cellosolve and water to obtain 4.8 g of intended 7-{2-[4-p-chlorobenzhydrylpiperazinyl-(1)]-ethyl}-theophylline hydrochloride (the yield being 42.5%).

Melting point: 250°–252° C.

Elementary Analysis Values as $C_{26}H_{29}O_2N_6CH.2HCl$: Calculated: C=55.16%, H=5.53%, N=14.85%. Found: C=55.19%, H=5.38%, N=14.87%.

TABLE 4

| Compound | | Class of Activity | Increase of flood flow (ml) | Duration of Action (minutes) | Dose (microgram/kg) |
|---|---|---|---|---|---|
| [structure: 7-(CH$_2$)$_4$-piperazinyl-CH(p-Cl-phenyl)$_2$ theophylline .2HCl] | vertebral artery | C | 65.4 | 1.52 | 10 |
| | femoral artery | C | 94.1 | 1.72 | 10 |
| [structure: 7-(CH$_2$)$_5$-piperazinyl-(o-CH$_3$-phenyl) theophylline .2HCl] | vertebral artery | A | 18.7 | 0.69 | 0.1 |
| | femoral artery | A | 8.5 | 0.76 | 0.1 |
| [structure: 7-(CH$_2$)$_5$-piperazinyl-(2,3-dimethylphenyl) theophylline .2HCl] | vertebral artery | B | 27.8 | 0.68 | 1 |
| | femoral artery | B | 84.5 | 1.89 | 1 |
| [structure: 7-(CH$_2$)$_6$-piperazinyl-(o-Cl-phenyl) theophylline .2HCl] | vertebral artery | A | 15.4 | 1.39 | 0.1 |
| | femoral artery | A | 107.9 | 2.16 | 0.1 |

The present invention will now be described in detail with reference to the following Examples that by no means limit the scope of the present invention.

EXAMPLE 1

Synthesis of 7-{2-[4-p-chlorobenzhydrylpiperazinyl-(1)-ethyl}-theopylline hydrochloride In benzene, 6.3 g of 7-(2-bromoethyl)theophylline, 5.7 g of 1-(p-chlorobenzhydryl)piperazine and 4.0 g of triethylamine are stirred under reflux for 18.5 hours. Triethylamine hydrochloride is removed by filtration and the filtrate is extracted with dilute hydrochloric acid. The extract is made alkaline by dilute sodium

EXAMPLE 2

Synthesis of 7-{4-[4-o-methoxyphenylpiperazinyl-(1)]-n-butyl}-thoephylline

In benzene, 6.9 g of 7-(4-bromo-n-butyl)theophylline, 3.8 g of o-methoxyphenylpiperazine and 4.0 g of triethylamine are stirred under reflux for 18 hours. The subsequent treatments are carried out in the same manner as described in Example 1. The obtained crude crystal is recrystallized from ethanol to obtain 3.8 g of intended 7-{4-[4-o-methoxyphenylpiperzinyl-(1)]n-butyl}-theophylline (the yield being 37.6%).

Melting Point: 117°–118° C.

Elementary Analysis Values as $C_{22}H_{30}O_3N_6$: Calculated: C=61.94%, H=7.10%, N=19.71%. Found: C=62.10%, H=7.21%, N=19.86%.

EXAMPLE 3

Synthesis of 7-{5-[4-o,m-dimethylphenylpiperazinyl-(1)-n-heptyl}-theophylline

In toluene, 9.9 g of 1-(5-bromo-n-heptyl)theophylline, 3.8 g of o,m-dimethylphenylpiperazine and 4.0 g of triethylamine are stirred under reflux for 11.5 hours, and the subsequent treatments are carried out in the same manner as described in Example 1. The obtained crude crystal is recrystallized from ethanol to obtain 4.3 g of intended 7-{5-[4-o,m-dimethylphenylpiperazinyl-(1)]-n-heptyl}-theophylline.

Meltint Point: 115°–117° C.

Elementary Analysis Values as $C_{24}H_{34}O_2N_6$: Calculated: C=65.71%, H=7.38%, N=19.16%. Found: C=65.42%, H=7.92%, N=19.31%.

EXAMPLE 4

Synthesis of 7-{7-[(3-methyl-4-m-methylphenyl)-piperazinyl-(1)]-n-heptyl}-theophylline hydrochloride In toluene, 7.8 g of 7-(7-bromo-n-heptyl)theophylline, 3.8 g of N-(m-methylphenyl)-2-methyl-N-piperazine and 4.0 g of triethylamine are stirred under reflux for 11 hours. The subsequent treatments are carried out in the same manner as described in Example 1 to obtain 10 g of a crude crystal. The obtained crude crystal is purified by silica gel chromatography and converted to a hydrochloride according to customary procedures to obtain 5.3 g of intended 7-{7-[3-methyl(4-m-methylphenyl)-piperazinyl-(1)-n-heptyl}-theophylline hydrochloride.

Melting point: 222°–265° C.

Elementary Analysis Values as $C_{26}H_{39}O_2N_6Cl_2 \cdot \frac{1}{2}H_2O$ Calculated: C=57.02%, H=7.38%, N=15.35%. Found: C=57.00%, H=7.88%, N=15.20%.

EXAMPLES 5 THROUGH 95

Compounds shown in Table 3 are prepared according to the method described in Example 1.

TABLE 5

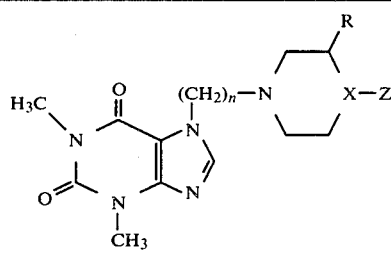

| Example No. | n | X | R | Z | Recrystallization Solvent | Melting Point (°C.) | Molecular Formula | Elementary Analysis Values (upper values: calculated values, lower values: found values) | | |
|---|---|---|---|---|---|---|---|---|---|---|
| | | | | | | | | C (%) | H (%) | N(%) |
| 5 | 2 | N | H | –⟨phenyl⟩ | ethanol | 228–234 (decomposition) | $C_{19}H_{24}O_2N_6 \cdot 2HCl$ | 51.70 51.53 | 9.45 9.16 | 19.04 18.70 |
| 6 | 3 | N | H | –⟨phenyl⟩ | methanol | 143–145 | $C_{20}H_{26}O_2N_6$ | 62.79 62.66 | 6.87 6.90 | 21.98 22.01 |
| 7 | 4 | N | H | –⟨phenyl⟩ | ethanol | 114–115 | $C_{21}H_{28}O_2N_6$ | 63.60 63.61 | 7.13 7.25 | 21.20 21.34 |
| 8 | 5 | N | H | –⟨phenyl⟩ | ethanol/ isopropyl ether | 112–113 | $C_{22}H_{30}O_2N_6$ | 64.35 64.44 | 7.38 7.49 | 20.47 20.43 |
| 9 | 6 | N | H | –⟨phenyl⟩ | ethanol/ isopropyl ether | 200–203 (decomposition) | $C_{23}H_{32}O_2N_6 \cdot 2HCl$ | 55.52 55.26 | 6.90 6.71 | 16.90 16.59 |

TABLE 5-continued $$\text{structure: 1,3-dimethylxanthine with 7-(CH}_2)_n\text{-N-piperidine(X-Z) with R substituent}$$

| Example No. | n | X | R | Z | Recrystallization Solvent | Melting Point (°C.) | Molecular Formula | Elementary Analysis Values (upper values: calculated values, lower values: found values) | | |
|---|---|---|---|---|---|---|---|---|---|---|
| | | | | | | | | C (%) | H (%) | N(%) |
| 10 | 2 | N | H | 2-CH$_3$-phenyl | ethanol | 149-150 | C$_{20}$H$_{20}$O$_2$N$_6$ | 62.80 / 62.52 | 6.85 / 6.85 | 21.98 / 21.81 |
| 11 | 3 | N | H | 2-CH$_3$-phenyl | ethanol | 114-116 | C$_{21}$H$_{28}$O$_2$N$_6$ | 63.60 / 63.26 | 7.13 / 7.21 | 21.20 / 20.75 |
| 12 | 5 | N | H | 2-CH$_3$-phenyl | ethanol/ isopropyl ether | 113-114 | C$_{22}$H$_{32}$O$_2$N$_6$ | 65.05 / 65.08 | 7.61 / 7.80 | 19.80 / 19.75 |
| 13 | 2 | N | H | 3-CH$_3$-phenyl | ethanol | 121-122 | C$_{20}$H$_{26}$O$_2$N$_6$ | 62.80 / 62.98 | 6.85 / 6.83 | 21.98 / 21.97 |
| 14 | 4 | N | H | 3-CH$_3$-phenyl | ethanol | 237-239 (decomposition) | C$_{22}$H$_{30}$O$_2$N$_6$·2HCl | 54.66 / 54.57 | 6.67 / 6.69 | 17.39 / 17.47 |
| 15 | 5 | N | H | 3-CH$_3$-phenyl | ethanol | 239-241 (decomposition) | C$_{23}$H$_{32}$O$_2$N$_6$·2HCl | 55.30 / 55.32 | 6.87 / 6.90 | 16.83 / 16.98 |
| 16 | 6 | N | H | 3-CH$_3$-phenyl | ethanol | 224-226 (decomposition) | C$_{24}$H$_{34}$O$_2$N$_6$·2HCl | 56.35 / 56.05 | 7.09 / 7.10 | 16.43 / 16.42 |
| 17 | 2 | N | H | 2,4-di-CH$_3$-phenyl | ethanol/ isopropyl ether | 103-106 | C$_{21}$H$_{28}$O$_2$N$_6$ | 63.61 / 63.64 | 7.12 / 7.03 | 21.20 / 21.05 |

TABLE 5-continued

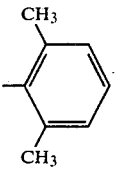

| Example No. | n | X | R | Z | Recrystallization Solvent | Melting Point (°C.) | Molecular Formula | Elementary Analysis Values (upper values: calculated values, lower values: found values) | | |
|---|---|---|---|---|---|---|---|---|---|---|
| | | | | | | | | C (%) | H (%) | N(%) |
| 18 | 3 | N | H | 2,6-(CH$_3$)$_2$-C$_6$H$_3$ | ethanol | 116–118 | C$_{22}$H$_{30}$O$_2$N$_6$ | 64.35 / 64.31 | 7.38 / 7.48 | 20.47 / 20.52 |
| 19 | 4 | N | H | 2,6-(CH$_3$)$_2$-C$_6$H$_3$ | ethanol | 275–276 (decomposition) | C$_{23}$H$_{32}$N$_6$O$_2$·HCl | 59.92 / 59.54 | 7.21 / 7.26 | 18.23 / 18.05 |
| 20 | 5 | N | H | 2,6-(CH$_3$)$_2$-C$_6$H$_3$ | ethanol | 136–138 | C$_{24}$H$_{34}$O$_2$N$_6$ | 65.71 / 66.00 | 7.83 / 7.94 | 19.16 / 19.13 |
| 21 | 6 | N | H | 2,6-(CH$_3$)$_2$-C$_6$H$_3$ | ethanol/ isopropyl ether | 167–170 (decomposition) | C$_{25}$H$_{30}$O$_2$N$_6$·2HCl | 57.14 / 56.75 | 7.30 / 7.50 | 15.99 / 16.44 |
| 22 | 2 | N | H | 2,6-(CH$_3$)$_2$-C$_6$H$_3$ | ethanol | 151–152 | C$_{21}$H$_{28}$O$_2$N$_6$ | 63.61 / 63.93 | 7.12 / 7.17 | 21.20 / 21.26 |
| 23 | 3 | N | H | 2,6-(CH$_3$)$_2$-C$_6$H$_3$ | ethanol | 153–155 | C$_{22}$H$_{30}$O$_2$N$_6$ | 64.36 / 64.08 | 7.38 / 7.46 | 20.48 / 20.10 |
| 24 | 4 | N | H | 2,6-(CH$_3$)$_2$-C$_6$H$_3$ | ethanol | 114–116 | C$_{23}$H$_{32}$O$_2$N$_6$ | 65.05 / 64.63 | 7.61 / 7.53 | 19.80 / 19.79 |

TABLE 5-continued

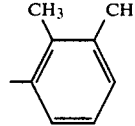

| Example No. | n | X | R | Z | Recrystallization Solvent | Melting Point (°C.) | Molecular Formula | Elementary Analysis Values (upper values: calculated values, lower values: found values) | | |
|---|---|---|---|---|---|---|---|---|---|---|
| | | | | | | | | C (%) | H (%) | N(%) |
| 25 | 5 | N | H | 2,3-(CH$_3$)$_2$-C$_6$H$_3$ | ethanol | 115–117 | C$_{24}$H$_{34}$O$_2$N$_6$ | 65.71 / 65.42 | 7.38 / 7.97 | 19.16 / 19.31 |
| 26 | 2 | N | H | 2,4-(CH$_3$)$_2$-C$_6$H$_3$ | ethanol | 140–141 | C$_{21}$H$_{28}$O$_2$N$_6$ | 63.61 / 63.46 | 7.12 / 6.96 | 21.20 / 21.12 |
| 27 | 3 | N | H | 2,4-(CH$_3$)$_2$-C$_6$H$_3$ | ethanol | 128–129 | C$_{22}$H$_{30}$O$_2$N$_6$ | 64.36 / 63.71 | 7.37 / 7.43 | 20.47 / 20.34 |
| 28 | 4 | N | H | 2,4-(CH$_3$)$_2$-C$_6$H$_3$ | ethanol | 251–252 (decomposition) | C$_{23}$H$_{34}$O$_2$N$_6$·HCl | 59.92 / 59.99 | 7.21 / 7.33 | 18.23 / 18.33 |
| 29 | 5 | N | H | 2,4-(CH$_3$)$_2$-C$_6$H$_3$ | ethanol/ isopropyl ether | 80–83 | C$_{24}$H$_{34}$O$_2$N$_6$· ½H$_2$O | 64.39 / 64.63 | 7.90 / 7.92 | 18.78 / 19.26 |
| 30 | 2 | N | H | 2-OCH$_3$-C$_6$H$_4$ | methyl cellosolve | 272–273 (decomposition) | C$_{20}$H$_{26}$O$_3$N$_6$· 2HCl | 50.95 / 50.76 | 6.00 / 5.68 | 17.83 / 17.52 |
| 31 | 3 | N | H | 2-OCH$_3$-C$_6$H$_4$ | methanol | 240–243 (decomposition) | C$_{21}$H$_{28}$O$_3$N$_6$· 2HCl | 51.95 / 51.76 | 6.24 / 6.15 | 17.31 / 16.98 |

TABLE 5-continued

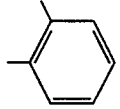

| Example No. | n | X | R | Z | Recrystallization Solvent | Melting Point (°C.) | Molecular Formula | Elementary Analysis Values (upper values: calculated values, lower values: found values) | | |
|---|---|---|---|---|---|---|---|---|---|---|
| | | | | | | | | C (%) | H (%) | N(%) |
| 32 | 4 | N | H | 2-OCH$_3$-phenyl | ethanol | 117–118 | C$_{22}$H$_{30}$O$_3$N$_6$ | 61.94 / 62.10 | 7.10 / 7.21 | 19.71 / 19.86 |
| 33 | 5 | N | H | 2-OCH$_3$-phenyl | ethanol | 120–121 | C$_{23}$H$_{32}$O$_3$N$_6$·H$_2$O | 60.23 / 60.50 | 7.49 / 7.20 | 18.33 / 18.37 |
| 34 | 6 | N | H | 2-OCH$_3$-phenyl | ethanol/ isopropyl ether | 213–215 (decomposition) | C$_{24}$H$_{34}$O$_3$N$_6$·2HCl | 54.63 / 54.61 | 6.89 / 6.58 | 15.93 / 15.49 |
| 35 | 2 | N | H | 3-OCH$_3$-phenyl | methyl cellosolve | 170–171 | C$_{20}$H$_{26}$O$_3$N$_6$ | 60.28 / 60.58 | 6.58 / 6.63 | 21.09 / 21.14 |
| 36 | 3 | N | H | 3-OCH$_3$-phenyl | methyl cellosolve | 161–163 | C$_{21}$H$_{28}$O$_3$N$_6$ | 61.13 / 61.12 | 6.85 / 6.85 | 20.38 / 20.58 |
| 37 | 4 | N | H | 3-OCH$_3$-phenyl | methanol | 211–212 (decomposition) | C$_{22}$H$_{30}$O$_3$N$_6$·HCl | 57.07 / 56.99 | 6.75 / 6.64 | 18.15 / 18.05 |
| 38 | 5 | N | H | 3-OCH$_3$-phenyl | ethanol | 120–121 | C$_{23}$H$_{32}$O$_3$N$_6$·H$_2$O | 60.23 / 60.50 | 7.49 / 7.20 | 18.33 / 18.37 |
| 39 | 6 | N | H | 3-OCH$_3$-phenyl | ethanol | 208–210 (decomposition) | C$_{24}$H$_{34}$O$_3$N$_6$·2HCl | 54.64 / 54.51 | 6.88 / 6.91 | 15.93 / 15.99 |
| 40 | 2 | N | H | 4-OCH$_3$-phenyl | ethanol | 155–156 | C$_{20}$H$_{26}$O$_3$N$_6$ | 60.28 / 60.12 | 6.58 / 6.59 | 21.09 / 21.05 |

TABLE 5-continued

| Example No. | n | X | R | Z | Recrystallization Solvent | Melting Point (°C.) | Molecular Formula | Elementary Analysis Values (upper values: calculated values, lower values: found values) | | |
|---|---|---|---|---|---|---|---|---|---|---|
| | | | | | | | | C (%) | H (%) | N(%) |
| 41 | 3 | N | H | —C₆H₄—OCH₃ | methyl cellosolve | 165–167 | C₂₁H₂₈O₃N₆ | 61.13 / 61.18 | 6.85 / 6.92 | 20.38 / 20.26 |
| 42 | 4 | N | H | —C₆H₄—OCH₃ | ethanol | 115–116 | C₂₂H₃₀O₃N₆ | 61.94 / 61.77 | 7.10 / 7.20 | 19.71 / 19.46 |
| 43 | 5 | N | H | —C₆H₄—OCH₃ | ethanol | 127–129 | C₂₃H₃₂O₃N₆ | 62.69 / 62.36 | 7.33 / 7.33 | 19.08 / 19.41 |
| 44 | 4 | N | H | o-Cl-C₆H₄ | ethanol/methyl cellosolve | 161–162 | C₁₉H₂₃O₂N₆Cl | 56.64 / 56.79 | 5.77 / 5.60 | 20.86 / 20.93 |
| 45 | 3 | N | H | o-Cl-C₆H₄ | ethanol | 121–122 | C₂₀H₂₅O₂N₆Cl | 57.61 / 57.64 | 6.06 / 5.96 | 20.16 / 20.23 |
| 46 | 2 | N | H | o-Cl-C₆H₄ | acetone | 117–119 | C₂₂H₂₉O₂N₆Cl | 59.37 / 59.53 | 6.58 / 6.80 | 18.89 / 19.11 |
| 47 | 2 | N | H | m-Cl-C₆H₄ | methyl cellosolve | 134–136 | C₁₉H₂₃O₂N₆Cl | 56.63 / 56.86 | 5.77 / 5.93 | 20.86 / 20.63 |
| 48 | 3 | N | H | m-Cl-C₆H₄ | ethanol | 109–111 | C₂₀H₂₅O₂N₆Cl | 57.61 / 57.55 | 6.06 / 6.35 | 20.16 / 19.00 |
| 49 | 4 | N | H | m-Cl-C₆H₄ | isopropanol/isopropyl ether | 96–98 | C₂₁H₂₇O₂N₆Cl | 58.52 / 58.82 | 6.33 / 6.41 | 19.51 / 19.26 |

TABLE 5-continued

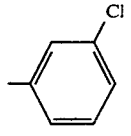

| Example No. | n | X | R | Z | Recrystallization Solvent | Melting Point (°C.) | Molecular Formula | Elementary Analysis Values (upper values: calculated values, lower values: found values) | | |
|---|---|---|---|---|---|---|---|---|---|---|
| | | | | | | | | C (%) | H (%) | N (%) |
| 50 | 5 | N | H | 3-Cl-C$_6$H$_4$ | ethanol/methanol | 151–154 | C$_{22}$H$_{31}$O$_2$N$_6$Cl$_3$.½ H$_2$O | 50.04 50.02 | 6.13 6.17 | 16.23 15.93 |
| 51 | 2 | N | H | 4-Cl-C$_6$H$_4$ | methyl cellosolve | 167–169 | C$_{19}$H$_{23}$O$_2$N$_6$Cl | 56.63 56.66 | 5.77 5.81 | 20.86 20.91 |
| 52 | 3 | N | H | 4-Cl-C$_6$H$_4$ | methyl cellosolve | 241–244 (decomposition) | C$_{20}$H$_{25}$O$_2$N$_6$Cl.2HCl | 49.03 48.66 | 5.57 5.20 | 17.16 16.84 |
| 53 | 4 | N | H | 4-Cl-C$_6$H$_4$ | ethanol | 107–109 | C$_{21}$H$_{27}$O$_2$N$_6$Cl | 58.52 58.77 | 6.33 6.38 | 19.50 19.44 |
| 54 | 5 | N | H | 4-Cl-C$_6$H$_4$ | isopropanol/ether | 127–130 | C$_{22}$H$_{29}$O$_2$N$_6$Cl.2HCl | 51.01 50.49 | 6.05 6.20 | 16.23 16.02 |
| 55 | 6 | N | H | 4-Cl-C$_6$H$_4$ | methanol | 110–111 | C$_{23}$H$_{31}$O$_2$N$_6$Cl | 60.17 60.20 | 6.82 6.96 | 18.31 18.68 |
| 56 | 2 | N | H | 2,3-Cl$_2$-C$_6$H$_3$ | methyl cellosolve | 146–147 | C$_{19}$H$_{22}$O$_2$N$_6$Cl$_2$ | 52.18 52.23 | 5.07 4.95 | 19.22 19.39 |
| 57 | 3 | N | H | 2,3-Cl$_2$-C$_6$H$_3$ | methyl cellosolve | 124–126 | C$_{20}$H$_{24}$O$_2$N$_6$Cl$_2$ | 53.21 53.50 | 5.37 5.32 | 18.62 18.52 |
| 58 | 4 | N | H | 2,3-Cl$_2$-C$_6$H$_3$ | methanol | 130–132 | C$_{21}$H$_{26}$O$_2$N$_6$Cl$_2$ | 54.19 54.44 | 5.64 5.73 | 18.06 18.21 |
| 59 | 3 | N | H | 4-F-C$_6$H$_4$ | methanol | 128–129 | C$_{20}$H$_{25}$O$_2$N$_6$F | 59.97 59.94 | 6.30 6.31 | 20.99 21.12 |

TABLE 5-continued

[Structure: 1,3-dimethylxanthine with 7-position substituent $-(CH_2)_n-N$(piperazine-like ring with R and X—Z)]

| Example No. | n | X | R | Z | Recrystallization Solvent | Melting Point (°C.) | Molecular Formula | C (%) | H (%) | N (%) |
|---|---|---|---|---|---|---|---|---|---|---|
| 60 | 4 | N | H | 4-F-phenyl | methanol | 223–226 (decomposition) | $C_{21}H_{27}O_2N_6F \cdot 2HCl$ | 51.74 / 51.65 | 6.00 / 5.84 | 17.25 / 16.94 |
| 61 | 5 | N | H | 4-F-phenyl | ethanol/methanol | 140–141 | $C_{22}H_{29}O_2N_6F$ | 61.65 / 61.32 | 6.83 / 6.77 | 19.61 / 19.67 |
| 62 | 3 | N | H | 3-$CF_3$-phenyl | methanol | 115–116 | $C_{21}H_{25}O_2N_6F_3$ | 55.98 / 56.46 | 5.60 / 5.71 | 18.66 / 19.26 |
| 63 | 4 | N | H | 3-$CF_3$-phenyl | ethanol/isopropyl ether | 215–218 | $C_{22}H_{26}O_2N_6F_3 \cdot 2HCl$ | 49.16 / 49.25 | 5.26 / 5.42 | 15.64 / 16.21 |
| 64 | 5 | N | H | 3-$CF_3$-phenyl | ethanol/isopropyl ether | 114–115 | $C_{23}H_{29}O_2N_6F_3$ | 57.72 / 57.55 | 6.12 / 6.13 | 17.56 / 17.71 |
| 65 | 2 | N | H | 2-pyridyl | methanol | 153–155 | $C_{18}H_{23}O_2N_7$ | 58.51 / 58.48 | 6.29 / 6.38 | 26.54 / 26.22 |
| 66 | 3 | N | H | 2-pyridyl | ethanol | 139–140 | $C_{19}H_{25}O_2N_7$ | 59.50 / 59.52 | 6.58 / 6.65 | 25.57 / 25.80 |
| 67 | 4 | N | H | 2-pyridyl | ethanol | 120–121 | $C_{20}H_{27}O_2N_7$ | 60.42 / 60.14 | 6.86 / 6.90 | 24.67 / 24.40 |
| 68 | 5 | N | H | 2-pyridyl | ethanol/isopropyl ether | 102–104 | $C_{21}H_{29}O_2N_7$ | 61.28 / 61.26 | 7.12 / 7.11 | 23.83 / 23.66 |

TABLE 5-continued

[Structure: 1,3-dimethylxanthine with 7-position substituent (CH₂)ₙ—N connected to a piperazine-type ring with substituent R and X—Z]

| Example No. | n | X | R | Z | Recrystallization Solvent | Melting Point (°C.) | Molecular Formula | Elementary Analysis Values (upper values: calculated values, lower values: found values) | | |
|---|---|---|---|---|---|---|---|---|---|---|
| | | | | | | | | C (%) | H (%) | N(%) |
| 69 | 6 | N | H | 2-pyridyl | ethanol | 96–97 | $C_{22}H_{31}O_2N_7$ | 62.08 / 62.01 | 7.36 / 7.46 | 23.04 / 23.35 |
| 70 | 3 | N | H | —CH(C₆H₅)₂ | methyl cellosolve | 252–254 | $C_{27}H_{32}O_2N_6 \cdot 2HCl$ | 59.44 / 59.28 | 6.29 / 6.42 | 15.41 / 15.59 |
| 71 | 4 | N | H | —CH(C₆H₅)₂ | ethanol/ methanol | 238–240 | $C_{23}H_{34}O_2N_6 \cdot 2HCl$ | 60.09 / 59.14 | 6.50 / 6.48 | 15.02 / 14.93 |
| 72 | 5 | N | H | —CH(C₆H₅)₂ | methyl cellosolve | 115–117 (decomposition) | $C_{29}H_{36}O_2N_6$ | 69.56 / 69.87 | 7.26 / 7.39 | 16.79 / 16.70 |
| 73 | 6 | N | H | —CH(C₆H₅)₂ | ethanol | 212–214 | $C_{30}H_{38}O_2N_6 \cdot 2HCl$ | 61.30 / 61.27 | 6.87 / 7.04 | 14.30 / 14.51 |
| 74 | 2 | N | H | —CH(C₆H₅)(4-ClC₆H₄) | methyl cellosolve | 250–252 | $C_{26}H_{29}O_2N_6Cl \cdot 2HCl$ | 55.16 / 55.19 | 5.53 / 5.38 | 14.85 / 14.87 |

TABLE 5-continued

[Structure: 1,3-dimethylxanthine with 7-position substituent $(CH_2)_n$-N-piperazine/piperidine ring bearing R and X-Z substituents]

| Example No. | n | X | R | Z | Recrystal- lization Solvent | Melting Point (°C.) | Molecular Formula | Elementary Analysis Values (upper values: calculated values, lower values: found values) | | |
|---|---|---|---|---|---|---|---|---|---|---|
| | | | | | | | | C (%) | H (%) | N(%) |
| 75 | 3 | N | H | -CH(4-Cl-phenyl)(phenyl) | methyl cellosolve | 222 (decomposition) | $C_{27}H_{31}O_2N_6Cl \cdot 2HCl \cdot H_2O$ | 54.22 53.64 | 5.91 5.92 | 14.06 14.09 |
| 76 | 4 | N | H | -CH(4-Cl-phenyl)(phenyl) | methanol | 208-210 | $C_{28}H_{33}O_2N_6Cl \cdot 2HCl$ | 56.61 55.97 | 5.95 6.04 | 14.15 13.92 |
| 77 | 5 | N | H | -CH(4-Cl-phenyl)(phenyl) | ethanol/ isopropyl ether | 117-119 | $C_{29}H_{35}O_2N_6Cl$ | 65.08 65.23 | 6.60 6.64 | 15.70 16.02 |
| 78 | 6 | N | H | -CH(4-Cl-phenyl)(phenyl) | ethanol | 201-203 | $C_{30}H_{37}O_2N_6Cl \cdot 2HCl \cdot \frac{1}{2}H_2O$ | 57.09 57.00 | 6.40 6.54 | 13.32 13.90 |
| 79 | 2 | N | -CH$_3$ | phenyl | ethanol | 128-130 | $C_{20}H_{26}O_2N_6$ | 62.80 62.73 | 6.85 6.87 | 21.98 21.91 |
| 80 | 4 | N | -CH$_3$ | phenyl | isopropanol | 99-100 | $C_{22}H_{30}O_2N_6$ | 64.36 64.51 | 7.37 7.47 | 20.47 20.87 |
| 81 | 5 | N | -CH$_3$ | phenyl | acetone/ isopropyl ether | 111-113 | $C_{21}H_{28}O_2N_6$ | 63.28 63.74 | 7.09 7.12 | 21.09 21.35 |

TABLE 5-continued

[Structure: theophylline-like core with (CH₂)ₙ—N—piperazine/piperidine—X—Z, R substituent]

| Example No. | n | X | R | Z | Recrystallization Solvent | Melting Point (°C.) | Molecular Formula | C (%) | H (%) | N (%) |
|---|---|---|---|---|---|---|---|---|---|---|
| 82 | 2 | N | —CH₃ | —C₆H₄—OCH₃ (p) | ethanol | 117–118 | C₂₁H₂₈N₆O₃ | 61.14 / 61.00 | 6.84 / 6.94 | 20.38 / 20.23 |
| 83 | 5 | N | —CH₃ | —C₆H₄—OCH₃ (p) | isopropanol | 85–87 | C₂₄H₃₁O₃N₆ | 63.82 / 63.56 | 6.93 / 7.69 | 18.61 / 18.63 |
| 84 | 2 | C | H | phenyl | methanol | 155–156 | C₂₀H₂₅O₂N₅ | 65.36 / 65.69 | 6.87 / 6.80 | 19.06 / 19.17 |
| 85 | 3 | C | H | phenyl | methyl cellosolve | 157–159 | C₂₁H₂₇O₂N₅ | 66.10 / 66.05 | 7.15 / 7.16 | 18.36 / 18.55 |
| 86 | 4 | C | H | phenyl | ethanol | 117–118 | C₂₂H₂₉O₂N₅ | 66.80 / 67.01 | 7.40 / 7.51 | 17.71 / 17.70 |
| 87 | 7 | N | —CH₃ | m-Cl-C₆H₄ | ethanol/ isopropyl ether | 200–204 | C₂₅H₃₅O₂N₆Cl·HCl·H₂O | 55.44 / 55.36 | 7.09 / 6.88 | 15.52 / 15.92 |
| 88 | 7 | N | H | 2,3-(CH₃)₂-C₆H₃ | hydrous ethanol | 239–241 | C₂₆H₃₇O₂N₆·2HCl·½H₂O | 57.02 / 57.46 | 7.38 / 7.45 | 15.35 / 15.77 |
| 89 | 8 | N | H | 2,4-(CH₃)₂-C₆H₃ | hydrous ethanol | 181–183 | C₂₇H₄₀N₆O₂·2HCl | 58.79 / 58.71 | 7.68 / 7.58 | 15.24 / 15.22 |
| 90 | 5 | N | H | 2,3-Cl₂-C₆H₃ | ethanol/ isopropyl ether | 112–114 | C₂₂H₂₆O₂N₆·HCl | 55.11 / 55.09 | 5.90 / 5.93 | 17.53 / 17.31 |

TABLE 5-continued

[Structure: theobromine with (CH2)n-N-piperazine-X-Z substituent, R group]

| Example No. | n | X | R | Z | Recrystallization Solvent | Melting Point (°C.) | Molecular Formula | C (%) | H (%) | N(%) |
|---|---|---|---|---|---|---|---|---|---|---|
| 91 | 7 | N | H | 4-Cl-phenyl (with CH3) | hydrous methanol | 223–226 (decomposition) | $C_{25}H_{35}O_2N_6Cl \cdot 2HCl$ | 53.90 / 53.49 | 6.17 / 6.60 | 15.09 / 15.50 |
| 92 | 10 | N | H | o-OCH3-phenyl | ethanol | 207–209 (decomposition) | $C_{28}H_{41}O_3N_6 \cdot 2HCl$ | 57.71 / 57.76 | 7.45 / 7.91 | 14.43 / 14.11 |
| 93 | 10 | N | H | 4-Cl-phenyl (with CH3) | ethanol | 211–213 (decomposition) | $C_{28}H_{41}O_2N_6Cl \cdot HCl$ | 59.45 / 59.31 | 7.50 / 7.50 | 14.80 / 14.69 |
| 94 | 10 | N | —CH3 | m-CH3-phenyl | methanol/ isopropyl ether | 211–214 (decomposition) | $C_{29}H_{46}O_2N_6 \cdot 2HCl \cdot 2H_2O$ | 56.38 / 56.12 | 8.17 / 7.76 | 13.60 / 13.46 |
| 95 | 10 | N | H | o,m-di-CH3-phenyl | methanol/ isopropyl ether | 187–190 (decomposition) | $C_{29}H_{44}O_2N_6 \cdot 2HCl$ | 59.87 / 59.42 | 7.99 / 7.96 | 14.45 / 14.09 |

EXAMPLE 96

Synthesis of 1-{4-[4-o,m-dimethylphenylpiperazinyl-(1)-n-butyl}-theobromine

In toluene, 9.5 g of 1-(4-bromo-n-butyl)theobromine, 3.8 g of o,m-dimethylphenylpiperazine and 4.0 g of triethylamine are stirred under reflux for 13 hours. Triethylamine hydrochloride is removed by filtration and the filtrate is extracted with dilute hydrochloric acid. The extract is made alkaline by dilute sodium hydroxide and is then extracted with chloroform. The chloroform layer is washed with water and dried with anhydrous potassium carbonate. The solvent is removed by distillation and the residual crude crystal is recrystallized from methyl cellosolve to obtain 3.7 g of intended 1-{4-[4-o,m-dimethylphenylpiperazinyl-(1)]-n-butyl}-theobromine (the yield being 43.64%).

Melting Point: 134°–135° C.

Elementary Analysis Values as $C_{23}H_{32}O_2N_6$: Calculated: C=65.05%, H=7.61%, N=19.80%. Found: C=65.11%, H=7.72%, N=19.46%.

EXAMPLE 97

Synthesis of 1-{5-[4-benzhydrylpiperazinyl-(1)]-n-pentyl}-theobromine hydrochloride In toluene, 7.9 g of 1-(5-bromo-n-pentyl)theobromine, 5.0 g of N-benzyhydrylpiperazine and 4 g of triethylamine are stirred under reflux for 30 hours. The subsequent treatments are carried out in the same manner as described in Example 96. The obtained crude crystal is converted to a hydrochloride according to customary procedures to obtain 4.7 g of intended 1-}5-[4-benzhydrylpiperazinyl-(1)]-n-pentyl}-theobromine hydrochloride (the yield being 40.9%).

Melting Point: 262°–264° C. (decomposition).
Elementary Analysis Values as $C_{29}H_{36}O_2N_6 \cdot 2HCl$:
Calculated: C=60.93%, H=6.71%, N=14.71%.
Found: C=60.57%, H=7.15%, N=14.65%.

EXAMPLE 98

Synthesis of
1-{7-[4-o-methoxyphenylpiperazinyl-(1)]-n-heptyl}-theobromine

In toluene, 7.5 g of 1-(7-bromo-n-heptyl)theobromine, 3.8 g of N-o-methoxyphenylpiperazine and 4.0 g of triethylamine are stirred under reflux for 11.5 hours, and the subsequent treatments are carried out in the same manner as described in Example 96. The obtained crude crystal is purified by silica gel chromatography to obtain 4.6 g of intended 1-7-[4-o-methoxyphenyl-piperazinyl(1)-n-heptyl-theobromine (the yield being 49.1%).
Melting Point: 97°–98° C.
Elementary Analysis Values as $C_{25}H_{36}O_3N_6$: Caculated: C=64.08%, H=7.74%, N=17.94%. Found: C=63.90%, H=7.67%, N=18.01%.

EXAMPLES 99 THROUGH 148

Compounds shown in Table 6 are prepared according to the method described in Example 96.

TABLE 6

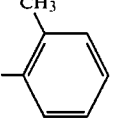

| Example No. | n | R | Z | Recrystallization Solvent | Melting Point (°C.) | Molecular Formula | Elementary Analysis Values (upper values: calculated values, lower values: found values) | | |
|---|---|---|---|---|---|---|---|---|---|
| | | | | | | | C (%) | H (%) | N (%) |
| 99 | 6 | H | 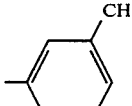 | ethanol | 197–198 (decomposition) | $C_{24}H_{34}N_6O_2 \cdot 2HCl \cdot 2H_2O$ | 52.65 52.64 | 7.01 7.10 | 15.35 15.28 |
| 100 | 2 | H | 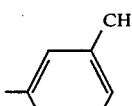 | ethanol | 251 (decomposition) | $C_{20}H_{26}O_2N_6 \cdot 2HCl$ | 52.75 52.41 | 6.21 6.11 | 18.46 18.31 |
| 101 | 5 | H | 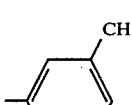 | ethanol | 133–135 | $C_{23}H_{32}O_2N_6$ | 65.05 65.03 | 7.61 7.62 | 19.80 19.82 |
| 102 | 6 | H | 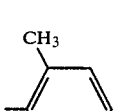 | ethanol | 206–208 (decomposition) | $C_{24}H_{34}O_2N_6 \cdot 2HCl \cdot 2H_2O$ | 52.65 53.10 | 7.01 6.91 | 15.35 15.44 |
| 103 | 2 | H | 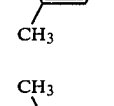 | ethanol | 151–153 | $C_{21}H_{28}O_2N_6$ | 63.60 63.60 | 7.13 7.05 | 21.20 21.28 |
| 104 | 3 | H |  | ethanol | 154–156 | $C_{22}H_{30}O_2N_6$ | 64.36 64.13 | 7.37 7.49 | 20.47 20.32 |

TABLE 6-continued

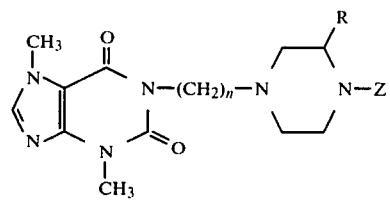

| Example No. | n | R | Z | Recrystallization Solvent | Melting Point (°C.) | Molecular Formula | C (%) | H (%) | N (%) |
|---|---|---|---|---|---|---|---|---|---|
| 105 | 4 | H | 2,6-dimethylphenyl | ethanol | 124–126 | $C_{23}H_{32}O_2N_6$ | 65.05 / 65.03 | 7.61 / 7.61 | 19.80 / 19.82 |
| 106 | 5 | H | 2,4,6-trimethylphenyl | ethanol | 121–123 | $C_{24}H_{34}O_2N_6$ | 65.71 / 65.68 | 7.38 / 7.73 | 19.16 / 19.36 |
| 107 | 2 | H | 2,6-dimethylphenyl | ethanol | 161–162 | $C_{21}H_{28}O_2N_6$ | 63.60 / 63.67 | 7.13 / 7.07 | 21.20 / 21.16 |
| 108 | 3 | H | 2,6-dimethylphenyl | ethanol | 124–126 | $C_{23}H_{30}O_2N_6$ | 64.36 / 63.65 | 7.37 / 7.20 | 20.47 / 20.32 |
| 109 | 4 | H | 2,6-dimethylphenyl | methyl cellosolve | 134–135 | $C_{23}H_{32}O_2N_6$ | 65.05 / 65.11 | 7.61 / 7.72 | 19.80 / 19.46 |
| 110 | 5 | H | 2,6-dimethylphenyl | ethanol/isopropyl ether | 118–120 | $C_{24}H_{34}O_2N_6$ | 65.71 / 65.65 | 7.38 / 7.95 | 19.16 / 18.94 |
| 111 | 6 | H | 2,6-dimethylphenyl | isopropanol/isopropyl ether | 91–93 | $C_{25}H_{36}O_2N_6$ | 66.34 / 65.84 | 8.02 / 8.31 | 18.57 / 18.50 |
| 112 | 2 | H | 2,4-dimethylphenyl | ethanol | 139–141 | $C_{21}H_{28}O_2N_6$ | 63.61 / 63.73 | 7.12 / 7.30 | 21.20 / 21.21 |

TABLE 6-continued

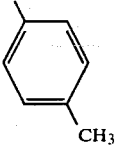

| Example No. | n | R | Z | Recrystallization Solvent | Melting Point (°C.) | Molecular Formula | Elementary Analysis Values (upper values: calculated values, lower values: found values) | | |
|---|---|---|---|---|---|---|---|---|---|
| | | | | | | | C (%) | H (%) | N (%) |
| 113 | 3 | H | 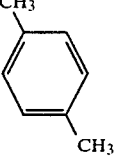 | ethanol | 137–139 | $C_{22}H_{30}O_2N_6$ | 64.36 64.19 | 7.37 7.44 | 20.47 20.36 |
| 114 | 4 | H | 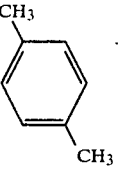 | ethanol | 148–150 | $C_{23}H_{32}O_2N_6$ | 65.05 64.44 | 7.61 7.52 | 19.80 19.70 |
| 115 | 5 | H | 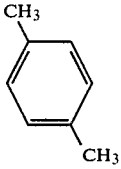 | isopropanol | 99–101 | $C_{24}H_{34}O_2N_6$ | 65.71 65.33 | 7.38 7.79 | 19.16 19.12 |
| 116 | 6 | H | 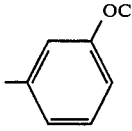 | ethanol/ isopropyl ether | 89–90 | $C_{25}H_{36}O_2N_6$ | 66.33 66.26 | 8.03 8.21 | 18.57 18.24 |
| 117 | 5 | H | 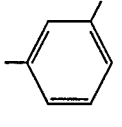 | ethanol | 165–166 (decomposition) | $C_{23}H_{32}O_3N_6 \cdot HCl$ | 57.91 57.81 | 6.97 7.19 | 17.62 17.21 |
| 118 | 6 | H | 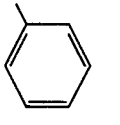 | ethanol/ methanol | 79–81 | $C_{24}H_{34}O_3N_6$ | 63.40 63.35 | 7.55 7.70 | 18.49 18.69 |
| 119 | 2 | H | 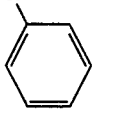 | ethanol | 122–124 | $C_{19}H_{23}O_2N_6Cl$ | 56.63 56.67 | 5.77 5.67 | 20.86 21.19 |
| 120 | 4 | H | Cl–phenyl | isopropanol/ isopropyl ether | 111–113 | $C_{21}H_{27}O_2N_6Cl \cdot \frac{1}{2}H_2O$ | 57.33 57.53 | 6.65 6.29 | 19.10 19.14 |

TABLE 6-continued

[Structure: 1,3-dimethylxanthine-like core with N—(CH$_2$)$_n$—N-piperazine-N—Z substituent, with R on piperazine ring]

| Example No. | n | R | Z | Recrystallization Solvent | Melting Point (°C.) | Molecular Formula | C (%) | H (%) | N (%) |
|---|---|---|---|---|---|---|---|---|---|
| 121 | 6 | H | 3-Cl-phenyl | isopropanol/methanol | 106–107 | C$_{23}$H$_{31}$O$_2$N$_6$Cl | 60.17 / 60.21 | 6.82 / 6.97 | 18.31 / 18.63 |
| 122 | 2 | —CH$_3$ | phenyl | methyl cellosolve | 176–178 | C$_{20}$H$_{26}$O$_2$N$_6$ | 62.79 / 63.19 | 6.87 / 6.89 | 21.98 / 22.03 |
| 123 | 3 | —CH$_3$ | phenyl | ethanol | 126–128 | C$_{21}$H$_{28}$O$_2$N$_6$ | 63.61 / 63.56 | 7.12 / 7.28 | 21.20 / 21.54 |
| 124 | 4 | —CH$_3$ | phenyl | ethanol | 120–122 | C$_{22}$H$_{30}$O$_2$N$_6$ | 64.35 / 64.81 | 7.38 / 7.47 | 20.47 / 20.37 |
| 125 | 5 | —CH$_3$ | phenyl | ethanol/isopropyl ether | 102–104 | C$_{23}$H$_{32}$O$_2$N$_6$ | 65.07 / 65.10 | 7.60 / 7.77 | 19.80 / 19.82 |
| 126 | 6 | —CH$_3$ | phenyl | ethanol | 101–103 | C$_{24}$H$_{34}$O$_2$N$_6$ | 65.71 / 65.64 | 7.38 / 7.95 | 19.16 / 19.19 |
| 127 | 2 | —CH$_3$ | 4-OCH$_3$-phenyl | isopropanol | 118–119 | C$_{21}$H$_{25}$O$_3$N$_6$·½H$_2$O | 60.27 / 60.73 | 6.28 / 6.81 | 20.09 / 20.15 |
| 128 | 3 | —CH$_3$ | 4-OCH$_3$-phenyl | methanol | 142–143 | C$_{22}$H$_{30}$O$_3$N$_6$ | 61.95 / 61.95 | 7.09 / 7.13 | 19.71 / 19.91 |
| 129 | 4 | —CH$_3$ | 4-OCH$_3$-phenyl | ethanol | 108–110 | C$_{23}$H$_{32}$O$_3$N$_6$ | 62.70 / 62.84 | 7.32 / 7.39 | 19.08 / 19.24 |
| 130 | 3 | H | 2,3-Cl$_2$-phenyl | methyl cellosolve | 162–163 | C$_{20}$H$_{24}$O$_2$N$_6$Cl$_2$ | 53.21 / 53.11 | 5.37 / 5.41 | 18.62 / 18.62 |

TABLE 6-continued

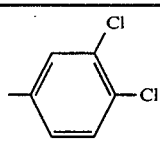

| Example No. | n | R | Z | Recrystallization Solvent | Melting Point (°C.) | Molecular Formula | Elementary Analysis Values (upper values: calculated values, lower values: found values) | | |
|---|---|---|---|---|---|---|---|---|---|
| | | | | | | | C (%) | H (%) | N (%) |
| 131 | 4 | H | 2,3-dichlorophenyl | methyl cellosolve | 140–142 | $C_{21}H_{26}O_2N_6Cl_2$ | 54.19<br>54.24 | 5.64<br>5.71 | 18.06<br>17.91 |
| 132 | 5 | H | 2,3-dichlorophenyl | methyl cellosolve | 132–134 | $C_{22}H_{28}O_2N_6Cl_2$ | 55.11<br>55.03 | 5.90<br>5.86 | 17.53<br>17.65 |
| 133 | 6 | H | 2,3-dichlorophenyl | ethanol | 144–145 | $C_{23}H_{30}O_2N_6Cl_2$ | 55.57<br>56.04 | 6.14<br>6.32 | 17.03<br>17.09 |
| 134 | 2 | H | —CH(C$_6$H$_5$)$_2$ | ethanol | 175–176 | $C_{26}H_{30}O_2N$ | 68.10<br>68.20 | 6.59<br>6.57 | 18.33<br>18.50 |
| 135 | 3 | H | —CH(C$_6$H$_5$)$_2$ | ethanol | 150–151 | $C_{27}H_{32}O_2N_6$ | 68.62<br>68.66 | 6.83<br>6.87 | 17.79<br>17.85 |
| 136 | 4 | H | —CH(C$_6$H$_5$)$_2$ | methyl cellosolve | 163–165 | $C_{28}H_{34}O_2N_6$ | 69.10<br>68.96 | 7.06<br>7.00 | 17.27<br>17.22 |
| 137 | 5 | H | —CH(C$_6$H$_5$)$_2$ | isopropanol | 262–264 | $C_{29}H_{36}O_2N_6\cdot 2HCl$ | 60.93<br>60.57 | 6.71<br>7.15 | 14.71<br>14.65 |

TABLE 6-continued

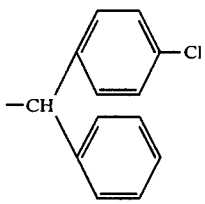

| Example No. | n | R | Z | Recrystallization Solvent | Melting Point (°C.) | Molecular Formula | Elementary Analysis Values (upper values: calculated values, lower values: found values) | | |
|---|---|---|---|---|---|---|---|---|---|
| | | | | | | | C (%) | H (%) | N (%) |
| 138 | 2 | H | 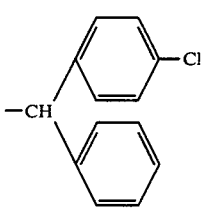 | methanol | 228–230 (decomposition) | $C_{26}H_{29}O_2N_6 \cdot 2HCl \cdot H_2O$ | 53.48 54.05 | 5.70 5.45 | 14.40 14.35 |
| 139 | 3 | H | 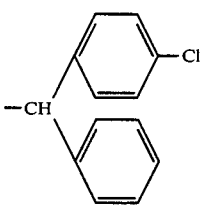 | methyl cellosolve | 194–195 (decomposition) | $C_{27}H_{31}O_2N_6 \cdot 2HCl \cdot 2H_2O$ | 52.64 53.21 | 5.74 5.95 | 13.64 13.74 |
| 140 | 4 | H | 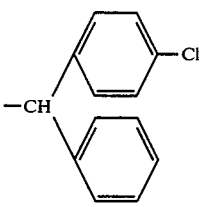 | ethanol/ isopropyl ether | 142–144 | $C_{28}H_{33}O_2N_6Cl$ | 64.53 64.76 | 6.40 6.52 | 16.13 16.16 |
| 141 | 5 | H | 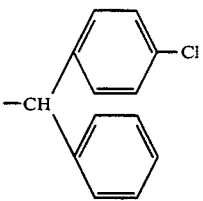 | methanol/ ethanol | 85–87 | $C_{29}H_{35}O_2N_6Cl \cdot 2HCl$ | 57.47 56.96 | 6.17 6.68 | 13.87 13.73 |
| 142 | 6 | H | 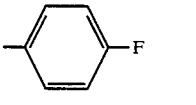 | ethanol/ isopropyl ether | 85–88 | $C_{30}H_{37}O_2N_6Cl \cdot 2HCl$ | 57.92 57.56 | 6.33 6.69 | 13.51 13.14 |
| 143 | 7 | H | 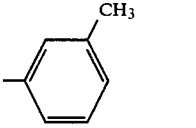 | acetone/ isopropyl ether | 81–83 | $C_{24}H_{33}O_2N_6F$ | 63.12 62.69 | 7.30 7.33 | 18.41 18.33 |
| 144 | 7 | H |  | purified by column chromatography (silica gel) | 90–91 | $C_{25}H_{36}O_2N_6$ | 66.34 66.24 | 8.02 8.03 | 18.57 18.54 |

TABLE 6-continued

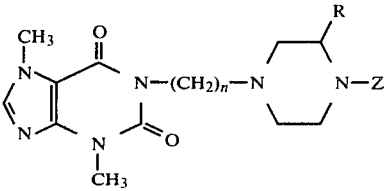

| Example No. | n | R | Z | Recrystallization Solvent | Melting Point (°C.) | Molecular Formula | C (%) | H (%) | N (%) |
|---|---|---|---|---|---|---|---|---|---|
| 145 | 8 | H | 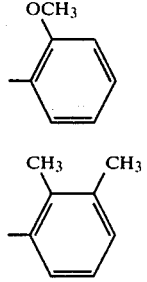 OCH₃ | hydrous ethanol | 173–177 | C₂₆H₃₈N₆O₃.2HCl.H₂O | 54.44<br>54.19 | 7.38<br>7.37 | 14.65<br>14.67 |
| 146 | 8 | H | 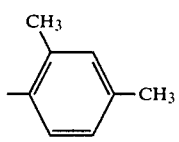 CH₃ CH₃ | hydrous ethanol | 228–230 | C₂₇H₄₀N₆O₂.HCl | 62.95<br>62.91 | 8.62<br>8.04 | 16.32<br>16.41 |
| 147 | 10 | H | 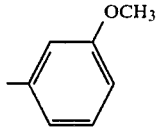 CH₃ CH₃ | hydrous ethanol | 147–150 | C₂₉H₄₄N₆O₂.2HCl.H₂O | 58.08<br>58.28 | 8.07<br>8.08 | 14.02<br>13.94 |
| 148 | 10 | —CH₃ | 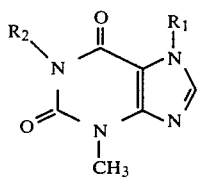 OCH₃ | ethanol | 154–157 | C₂₉H₄₄N₆O₃.2HCl.½H₂O | 57.44<br>57.32 | 7.81<br>7.92 | 13.86<br>13.84 |

What is claimed is:
1. A compound having the formula

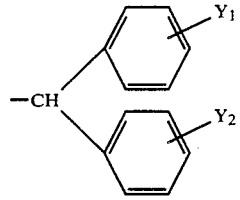

in which one of $R_1$ and $R_2$ is methyl and the other of $R_1$ and $R_2$ has the formula

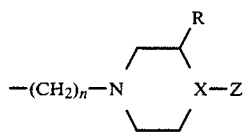

wherein R is hydrogen or lower alkyl; Z is pyridyl and or

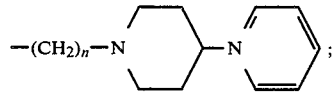

in which $Y_1$ and $Y_2$, which are the same or different, are hydrogen, lower alkyl, lower alkoxy, trifluoromethyl or halogen; X is C; and n is an integer of from 2 to 10; with the proviso that when $R_1$ is methyl, $R_2$ is not $$-(CH_2)_n-N\underset{\phantom{x}}{\overbrace{\phantom{xxxx}}}N\underset{\phantom{x}}{\overbrace{\phantom{xxxx}}};$$

or a pharmaceutically acceptable salt thereof.

2. A compound having the formula

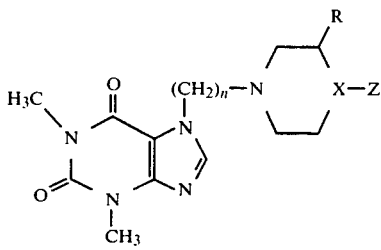

wherein R is hydrogen or lower alkyl; Z is selected from the group consisting of (a)

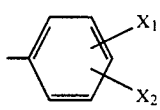

in which $X_1$ and $X_2$, which are the same or different, are hydrogen, lower alkyl, lower alkoxy, trifluoromethyl or halogen, (b) pyridyl and (c)

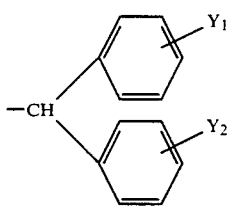

in which $Y_1$ and $Y_2$, which are the same or different, are hydrogen, lower alkyl, lower alkoxy, trifluoromethyl or halogen; X is C; and n is an integer of from 2 to 10; or a pharmaceutically acceptable salt thereof.

3. A compound having the formula

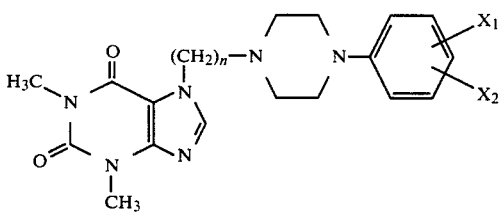

in which $X_1$ and $X_2$, which are the same or different, are hydrogen, lower alkyl, lower alkoxy, trifluoromethyl or halogen; and n is an integer of from 2 to 10; or a pharmaceutically acceptable salt thereof.

4. A compound as claimed in claim 3 in which n is 4, $X_1$ is m-methoxy and $X_2$ is hydrogen.

5. A composition as claimed in claim 3 in which n is 4, $X_1$ is p-chloro and $X_2$ is hydrogen.

6. A pharmaceutical composition which comprises a therapeutically effective amount of a compound as defined in claim 1, for vasodilating purposes, in combination with a pharmacologically acceptable carrier.

7. A pharmaceutical composition which comprises a therapeutically effective amount of a compound as defined in claim 1, for analgesic purposes, in combination with a pharmacologically acceptable carrier.

8. A method for treating a subject suffering from blood circulatory insufficiency which comprises administering to the subject a pharmaceutical composition as defined in claim 6.

9. A method for treating a subject suffering from a pain which comprises administering to the subject a pharmaceutical composition as defined in claim 7.

10. A compound of the formula

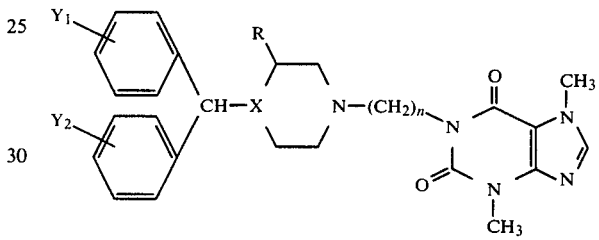

wherein R is hydrogen or lower alkyl, and $Y_1$ and $Y_2$, which are the same or different, are hydrogen, lower alkyl, lower alkoxy, trifluoromethyl or halogen; X is C; and n is an integer of from 2 to 10; or a pharmaceutically acceptable salt thereof.

11. A pharmaceutical composition which comprises a therapeutically effective amount of a compound as defined in claim 2, for vasodilating purposes, in combination with a pharmacologically acceptable carrier.

12. A pharmaceutical composition which comprises a therapeutically effective amount of a compound as defined in claim 2, for analgesic purposes, in combination with a pharmacologically acceptable carrier.

13. A method for treating a subject suffering from blood circulatory insufficiency which comprises administering to the subject a pharmaceutical composition as defined in claim 11.

14. A method for treating a subject suffering from a pain which comprises administering to the subject a pharmaceutical composition as defined in claim 12.

* * * * *

UNITED STATES PATENT AND TRADEMARK OFFICE
CERTIFICATE OF CORRECTION

PATENT NO. : 4 564 617

DATED : January 14, 1986

INVENTOR(S) : Hachiro Sugimoto et al

It is certified that error appears in the above-identified patent and that said Letters Patent is hereby corrected as shown below:

Column 51, line 61; delete "and".

Signed and Sealed this

Twenty-seventh Day of May 1986

[SEAL]

Attest:

DONALD J. QUIGG

Attesting Officer

Commissioner of Patents and Trademarks